(12) United States Patent
Wachtel

(10) Patent No.: US 7,252,087 B2
(45) Date of Patent: Aug. 7, 2007

(54) POWDER INHALER

(75) Inventor: Herbert Wachtel, Bingen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 10/979,943

(22) Filed: Nov. 2, 2004

(65) Prior Publication Data

US 2005/0279357 A1    Dec. 22, 2005

Related U.S. Application Data

(60) Provisional application No. 60/532,226, filed on Dec. 23, 2003.

(30) Foreign Application Priority Data

Nov. 8, 2003    (DE) .............................. 103 52 277

(51) Int. Cl.
*A61M 15/00*    (2006.01)
*B65D 1/09*    (2006.01)

(52) U.S. Cl. ........................... 128/203.21; 128/203.15; 206/528

(58) Field of Classification Search ........... 128/200.23, 128/203.15, 203.19, 203.21, 202.27; 206/528, 206/532, 531, 530, 534
See application file for complete search history.

(56) References Cited

U.S. PATENT DOCUMENTS

| | | | |
|---|---|---|---|
| 4,446,862 A | | 5/1984 | Baum et al. |
| 4,860,740 A | | 8/1989 | Kirk et al. |
| 4,884,565 A | * | 12/1989 | Cocozza ................ 128/203.21 |
| 5,207,217 A | * | 5/1993 | Cocozza et al. ....... 128/203.21 |
| 5,542,411 A | | 8/1996 | Rex |
| 5,685,294 A | | 11/1997 | Gupte et al. |
| 5,947,118 A | * | 9/1999 | Hochrainer et al. ... 128/203.15 |
| 5,964,417 A | * | 10/1999 | Amann et al. .............. 239/338 |
| 6,186,141 B1 | * | 2/2001 | Pike et al. ............. 128/203.12 |

(Continued)

FOREIGN PATENT DOCUMENTS

AT    221 414    5/1962

(Continued)

OTHER PUBLICATIONS

English Abstract: SU 1648842—WPIDS 1992-121992 [15].

(Continued)

*Primary Examiner*—Teena Mitchell
(74) *Attorney, Agent, or Firm*—Michael P. Morris; Mary-Ellen M. Devlin; Wendy Petka

(57) ABSTRACT

An inhaler for inhaling powdered medicament from capsules is described. Once the capsule has been placed in the capsule holder (3), the patient can press an actuating member (8), which interacts with at least one pin (9) adapted to be pushed into the capsule holder (3), causing the medicament to be released. In a preferred embodiment, the actuating member (8) is constructed as a multi-functional actuating member (8*a*) wherein, in a first functional position, the closure element (6) can be disengaged from the lower part (1) in order to pivot the cover (5), and wherein, in a second functional position, the mouthpiece (4) engaging with the plate (2) can be released from the plate (2) in such a way that the mouthpiece (4) can be pivoted away from the lower part (1).

6 Claims, 4 Drawing Sheets

U.S. PATENT DOCUMENTS

| | | | |
|---|---|---|---|
| 6,367,473 B1* | 4/2002 | Kafer | 128/203.21 |
| 6,606,992 B1* | 8/2003 | Smith et al. | 128/203.15 |
| 6,615,827 B2* | 9/2003 | Greenwood et al. | 128/200.23 |
| 6,848,443 B2* | 2/2005 | Schmidt et al. | 128/200.23 |
| 6,907,880 B1* | 6/2005 | Heckenmuller et al. | 128/203.15 |
| 2001/0020472 A1* | 9/2001 | Horlin | 128/203.15 |
| 2003/0000523 A1* | 1/2003 | Citterio | 128/203.15 |
| 2003/0070679 A1 | 4/2003 | Hochrainer et al. | |
| 2003/0235538 A1 | 12/2003 | Zierenberg | |
| 2004/0173211 A1* | 9/2004 | Kladders et al. | 128/203.15 |
| 2005/0084457 A1 | 4/2005 | Hochrainer et al. | |

FOREIGN PATENT DOCUMENTS

| | | |
|---|---|---|
| DE | 19 34 956 | 1/1971 |
| DE | 39 27 170 | 2/1991 |
| EP | 0 028 162 | 5/1981 |
| EP | 0 129 985 A1 | 1/1985 |
| FR | 1 510 968 | 10/1967 |
| FR | 221 68 06 | 8/1974 |
| FR | 241 81 61 | 9/1979 |
| GB | 206 43 34 | 6/1981 |
| GB | 206 43 36 | 6/1981 |
| SU | 1648842 | 4/1989 |
| WO | WO 82/01470 A1 | 5/1982 |
| WO | WO 91/02558 A1 | 3/1991 |
| WO | WO 91/06333 A1 | 5/1991 |
| WO | WO 92/03175 | 3/1992 |
| WO | WO 94/06498 A1 | 3/1994 |
| WO | WO 02/098874 | 12/2002 |
| WO | WO 03/084502 | 10/2003 |

OTHER PUBLICATIONS

English Abstract: DE 39 27 170—WPIDS 1991-058894 [09].
English Abstract: FR 241 81 61—WPIDS 1979-88021B [49].
English Abstract: FR 221 68 06—WPIDS 1974-L1909V [48].

* cited by examiner

POWDER INHALER

RELATED APPLICATIONS

Benefit of U.S. Provisional Application Ser. No. 60/532,226, filed on Dec. 23, 2003, is hereby claimed, and which application is incorporated herein in its entirety.

BACKGROUND OF THE INVENTION

The invention relates to an inhaler for inhaling powdered medicament from capsules which are inserted in a capsule holder arranged in the inhaler before use. After the capsule has been placed in the capsule holder the patient can press an actuating member, which can be set in motion from a resting position and thereby interacts with at least one pin adapted to be pushed into the capsule holder. Using the minimum of one pin the capsule is pierced and the medicament is released.

An inhaler of this kind is described for example in EP 0 703 800 B1 or EP 0 911 047 A1. The inhaler known from the above-mentioned specifications comprises a dish-shaped lower part and an equally dish-shaped cover which fits it, the two parts being adapted to be flipped apart for use by means of a hinge provided at the edge region. Engaging between the lower part and the cover in the hinge are a mouthpiece which can also be flipped out and a plate located below it with a capsule holder provided underneath. After the individual parts have been opened out the patient can place a capsule filled with medicament in the capsule holder, pivot the plate with the capsule holder and the mouthpiece back into the lower part and pierce the capsule by means of a spring-loaded actuating member projecting laterally from the lower part. Sucking on the mouthpiece then causes the medicament to be delivered to the respiratory tract of the patient being treated.

The intention is to improve the known inhalers further in terms of their handling.

BRIEF DESCRIPTION OF THE FIGURES

FIG. 2: is an exploded view of an embodiment with operating windows in the lower part which are capable of being pressed in;

DETAILED DESCRIPTION OF INVENTION

Figure 1:
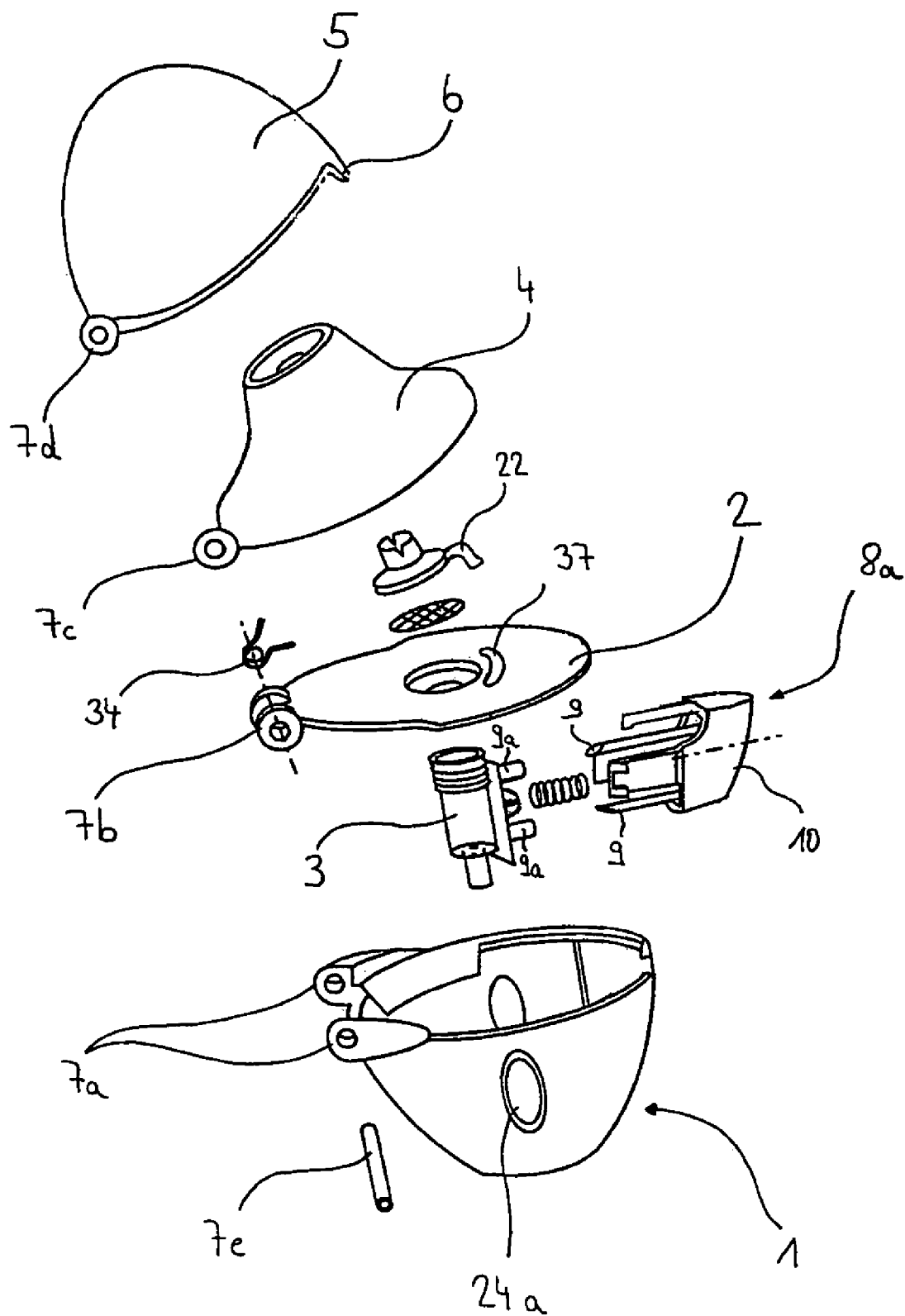
FIG. 1: is an exploded view with multi-functional actuating member of an embodiment with main body and thrust projection mounted thereon.

This aim is achieved according to the invention with an inhaler according to a first embodiment wherein the actuating member is constructed as a multi-functional actuating member by means of which, in a first functional position, the closure element can be disengaged from the lower part in order to pivot the cover, and with which in a second functional position the mouthpiece engaging with the plate can be released from the plate such that the mouthpiece can be pivoted away from the lower part.

The essential advantage of the invention is that the forces for releasing the cover and mouthpiece from mechanical engagement are not introduced directly through the cover or the mouthpiece, but through the multi-functional actuating member. This ensures safe and rapid opening of the cover and mouthpiece to make the inhaler ready for use. This is of major importance particularly at the start of an asthma attack. The actual opening movement of the cover can then be done by the patient, as before, by acting on the cover.

As the forces required for releasing the cover and mouthpiece components are significantly lower, there is no need to provide gripping aids. By gripping aids are meant, for example, depressions or grooves, which may have the disadvantage of attracting dirt. By dispensing with these gripping aids, in addition to improving the optical appearance, the hygiene conditions are also improved. This is particularly important in the area around the mouthpiece, as this component is placed in the oral cavity when the inhaler is used.

In a preferred embodiment, to assist the opening movement, spring elements may be disposed between the cover and lower part or mouthpiece and lower part, which are of suitable dimensions to allow the cover and/or mouthpiece to snap open.

Preferably the multi-functional actuating member is displaceably mounted on the plate or capsule holder. The plate and/or the capsule holder thus form(s) an abutment for the multi-functional actuating member, which slides along the plate as it moves from the resting position into the desired functional position and is thereby guided by means of a guide rail, for example.

In a favourable embodiment the multi-functional actuating member is spring-loaded. The restoring force which is already present in the resting position ensures that after the inhaler has been used the multi-functional actuating member is returned to the resting position and is thus ready for the next operation of loading with a new capsule and the next inhalation process.

Advantageously the multi-functional actuating member comprises a main body and two parallel guide arms engaging thereon. The guide arms project into the lower part and by means of corresponding built-in parts, for example with guide sleeves arranged on the outside of the capsule holder, serve to guide the multi-functional actuating member during the movement from the resting position into the respective functional positions and back into the resting position.

The guide arms may comprise end stops at their end remote from the main body, which abut on the guide sleeves in the resting position. In this way the multi-functional actuating member is put under tension.

In a preferred embodiment the main body comprises an upper and a lateral grooved surface. However, unlike in the prior art, these surfaces do not abut on the cover and especially not on the mouthpiece, but only on the main body of the multi-functional actuating member outside the inhaler and therefore do not come near the patient's mouth. In addition, the grooved surfaces may be smaller in area while still guaranteeing safe and rapid use of the inhaler.

Advantageously the upper grooved surface in the resting position has a recess in its region close to the cover for accommodating the closure element of the cover. Within the recess at least the side wall directed towards the lateral grooved surface may be inclined so that as the main body is pushed in, this side wall forms a sliding surface for the closure element and in this way the closure element together with the cover is lifted out of the latched position.

In the first particularly favourable embodiment described hitherto for releasing the mouthpiece the multi-functional actuating member comprises a thrust projection acting on the main body and a retaining lug mounted on the mouthpiece and engaging behind the plate, the thrust projection being aligned so that as it reaches the second functional position its front edge makes contact with the retaining lug. As the main body is pushed further forward the thrust projection pushes the preferably flexible retaining lug further back until the latter slides out of the opening in the fixed plate and releases the mouthpiece.

In a second preferred embodiment for releasing the mouthpiece the multi-functional actuating member comprises a pivot member pivotably mounted on a main body, on which is provided an impact cam projecting into the inhaler, and a retaining arm co-operating with the impact cam and mounted on the lower part, which in the closed position engages behind the mouthpiece through the plate, the impact cam projecting laterally past the retaining arm in the resting position. Preferably, the impact cam passes through an opening in the main body. In order to open the mouthpiece the patient swivels the pivot member and hence the impact cam as well, which, travelling along a path in the shape of an arc of a circle on the inside of the inhaler, comes up against the retaining arm connected to the mouthpiece and as more pressure is applied bends this arm. As a result the retaining arm which is preferably provided with a retaining hook slides out of the mouthpiece, thereby releasing the latter.

In an advantageous embodiment the impact cam is eccentrically mounted on the pivot member. This arrangement allows force to be transmitted as directly as possible to the retaining arm, depending on the mounting of the latter.

Alternatively to the embodiments described above for releasing the mouthpiece, at least one operating window with functional elements formed thereon may be provided in the lower part, the minimum of one operating window being adapted to be pressed into the lower part in guided and spring-loaded manner and by means of the functional elements releases the mouthpiece engaging with the plate from said plate. In this embodiment the assembly around the actuating member takes over the releasing of the cover, while the push-button in the lower part constructed as an operating window together with other components initiates the release of the mouthpiece by the patient. The operating windows enable the patient to check whether a capsule containing the medicament has been placed in the capsule holder.

Preferably, operating windows are arranged opposite in the lower part. If they are joined together in the manner of a clasp, a restoring force inherent in the material is produced, by an appropriate choice of material, so that no other spring elements are needed.

Advantageously the functional elements comprise hooks and retaining elements formed to complement them, the hooks being integrally formed with the minimum of one window and optionally extending as crosspieces in the direction of the mouthpiece. In the mouthpiece are found, in turn, the retaining elements, for example eyelets or retaining collars, in which the hooks can engage and thereby latch the mouthpiece. When the minimum of one operating window is pressed in, the hook also yields towards the interior of the lower part, so that the hook slides out of the retaining element and the mouthpiece can be flipped out.

Advantageously the plate latched to the lower part can be detached from the lower part so that the plate can be pivoted away from the lower part. The engagement between plate and lower part can be achieved using the retaining flaps mentioned earlier.

It is also possible to construct the inhaler according to all the embodiments so that the actuating member having the minimum of one pin which can penetrate into the capsule holder is attached to the plate such that it can be released from the lower part and swivelled away together with the plate latched to the lower part.

To assist in the understanding of the invention it will now be described more fully by reference to the three Figures provided herein.

FIG. 1 shows the inhaler in an exploded view. The essential assemblies are the lower part 1 which accommodates the plate 2 and is covered by the latter, the mouthpiece 4 which can be latched to the lower part 1 via the retaining lug 22 and the cover 5 which is formed to complement the lower part 1.

In the closed position of the inhaler the closure element 6 engages on the plate 2 and is held there by frictional engagement. It is also possible to obtain interlocking engagement by the provision of bead-like structures. For the closure element 6 to engage on the plate 2, the main body 10 of the multi-functional actuating member 8a comprises a recess 15, as can be seen most clearly from the enlarged view in FIG. 1a. The recess 15 is provided with an inclined side wall 16 and is located in the area 14 of the upper grooved surface 12 nearest the cover. For particularly reliable operation the multi-functional actuating member 8a is also provided with a lateral grooved surface 13.

To open the cover 5 first of all the multi-functional actuating member 8a is pushed forward into a first functional position. The closure element 6 then makes contact with the inclined side wall 16, which acts as a sliding surface 17 as the main body 10 continues to advance and ensures that the cover 5 is released.

The lower part 1 is cup-shaped and accommodates the whole of the capsule holder 3 arranged on the underside of the plate 2. However, in order to insert a capsule filled with medicament (not shown) the mouthpiece 4 must also be flipped out of the way. In the embodiment according to FIG. 1 this is done by pressing the multi-functional actuating member 8a further into a second functional position. A thrust projection 21 mounted on the main body 10 and aligned in the direction of movement of the main body 10 makes contact, by means of its front edge 23 (FIG. 1a) underneath the plate 2, with a retaining lug 22 projecting through the plate 2, fixedly mounted on the mouthpiece 4. The plate 2 comprises a retaining lug opening 37 in the region where the retaining lug 22 projects through.

As a result of the advancing movement of the thrust projection 21 the retaining lug 22 bends and escapes through the retaining lug opening 37, thereby pivoting the mouthpiece 4 away. This pivoting movement is assisted by an elastic spring 34.

In this opened position of the cover 5 and mouthpiece 4 the capsule can be placed in the capsule holder 3. For releasing the active substance two perpendicularly offset, parallel pins 9 are mounted on the main body, moving continuously as the main body 10 is pushed in towards the capsule (not shown) and perforating it. The perforation process can be observed through an inspection window 24a. Then the mouthpiece 4 is swivelled back again.

In the capsule holder 3 there are tubular pin passages 9a which are aligned axially in accordance with the direction of movement of the pins 9. On the one hand these ensure that the pins are correctly aimed at the capsule (not shown) and on the other hand they provide additional guidance of the multi-functional actuating member 8a. However, the essential guiding is done by two guide arms 11a, 11b arranged laterally on the main body 10. The guide arms 11a, 11b also have the task of holding the multi-functional actuating member 8*a* under spring bias. For this purpose the guide arms 11*a*, 11*b* are provided at their end remote from the main body 19 with end stops 20 which abut on the guide sleeves 18*a*, 18*b* in the resting position of the multi-functional actuating member 8*a*. The guide sleeves 18*a*, 18*b* are located on the outside of the capsule holder 3. Between the pins 9 is arranged a helical spring 38 which extends parallel to the pins 9 in its axial direction, the helical spring 38 being matched to the length of the guide arms 11*a*, 11*b* such that the multi-functional actuating member 8*a* is under tension even in the resting position.

The individual assemblies made up of the lower part 1, plate 2, mouthpiece 4 and cover 5 are connected by means of hinge recesses 7*a*, 7*b*, 7*c* 7*d* and a hinge bolt 7*e*.

Figure 2:
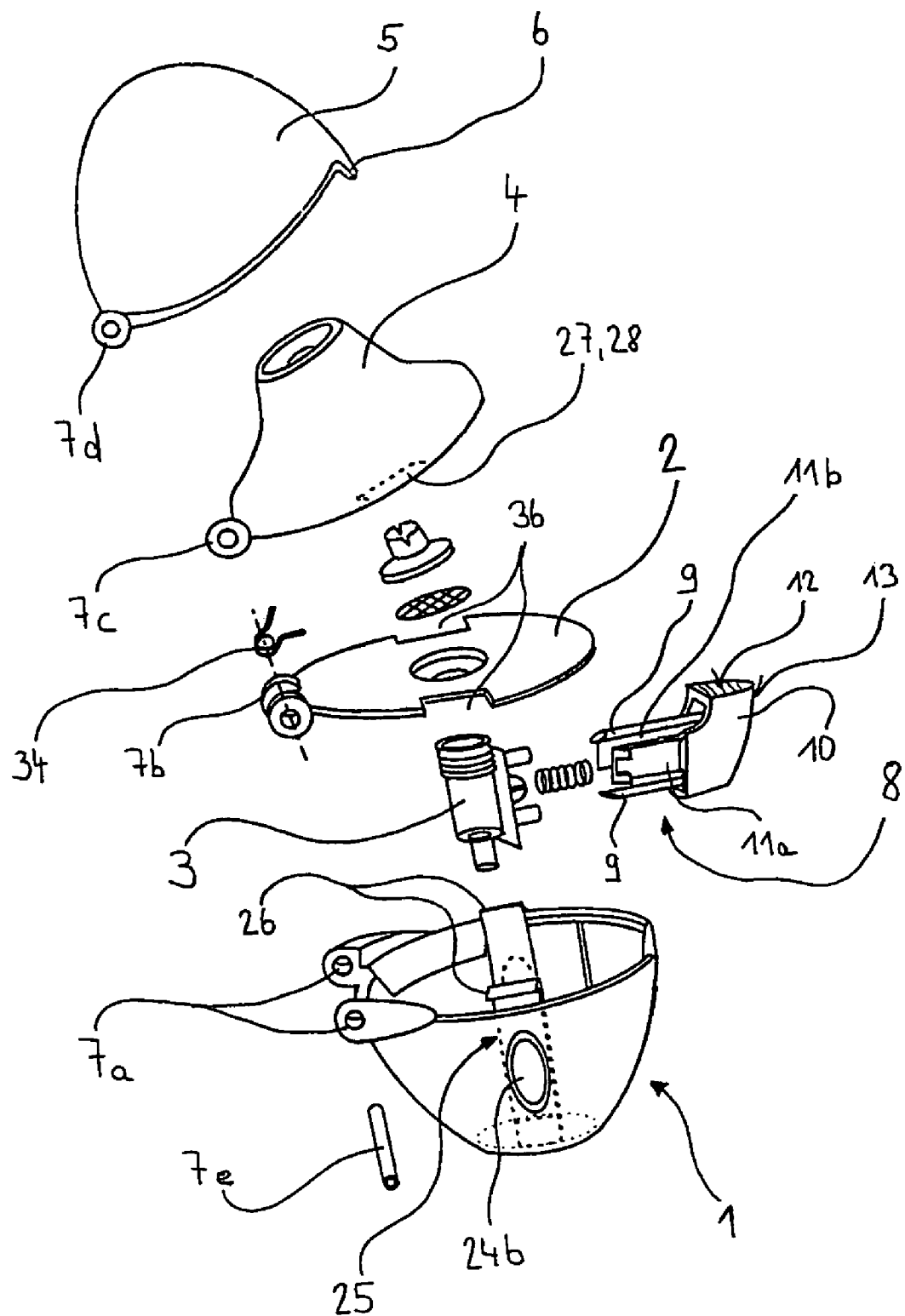

FIG. 2 shows a view similar to FIG. 1, wherein the opening of the cover 5 occurs as the first functional position is reached by actuating the main body 10 of the actuating member 8, similar to the embodiment shown in FIG. 1.

Once the cover 5 has been opened it is necessary to flip the mouthpiece 4 out of the way as well so that a capsule filled with medicament (not shown) can be placed in the capsule holder 3. For this purpose, the patient presses the operating window 24*b* provided on both sides in the lower part 1. As a result of the pressing action on the operating window 24*b* the functional elements 25, which are formed in FIG. 2 as upright posts integral with the window, bend inwards into the cavity of the lower part 1. On the ends of the functional elements there are hooks 26 which project outwards beyond the lower part 1 and when the plate 2 is closed make it possible to engage in the retaining elements 27 located on the inside of the mouthpiece 4 when said mouthpiece 4 is located on the plate 1. As for the mouthpiece 4 which has to be flipped out of the way, when a compressive force is applied to the operating window 24*b* the hooks 26 slide out of the retaining elements 27, which consist of a retaining collar 28, as in the case shown.

When the capsule (not shown) has been placed in the capsule holder 3 the mouthpiece 4 is swivelled back until it latches with the hooks 26 protruding through the hook passage 36. Then the capsule (not shown) can be pierced by pressing the main body 10. For this, two parallel pins 9 secured to the main body 10 project towards the capsule holder 3. After use the cover 5 is closed again. Meanwhile, the closure element 6 latches on the plate 2.

Figure 3:
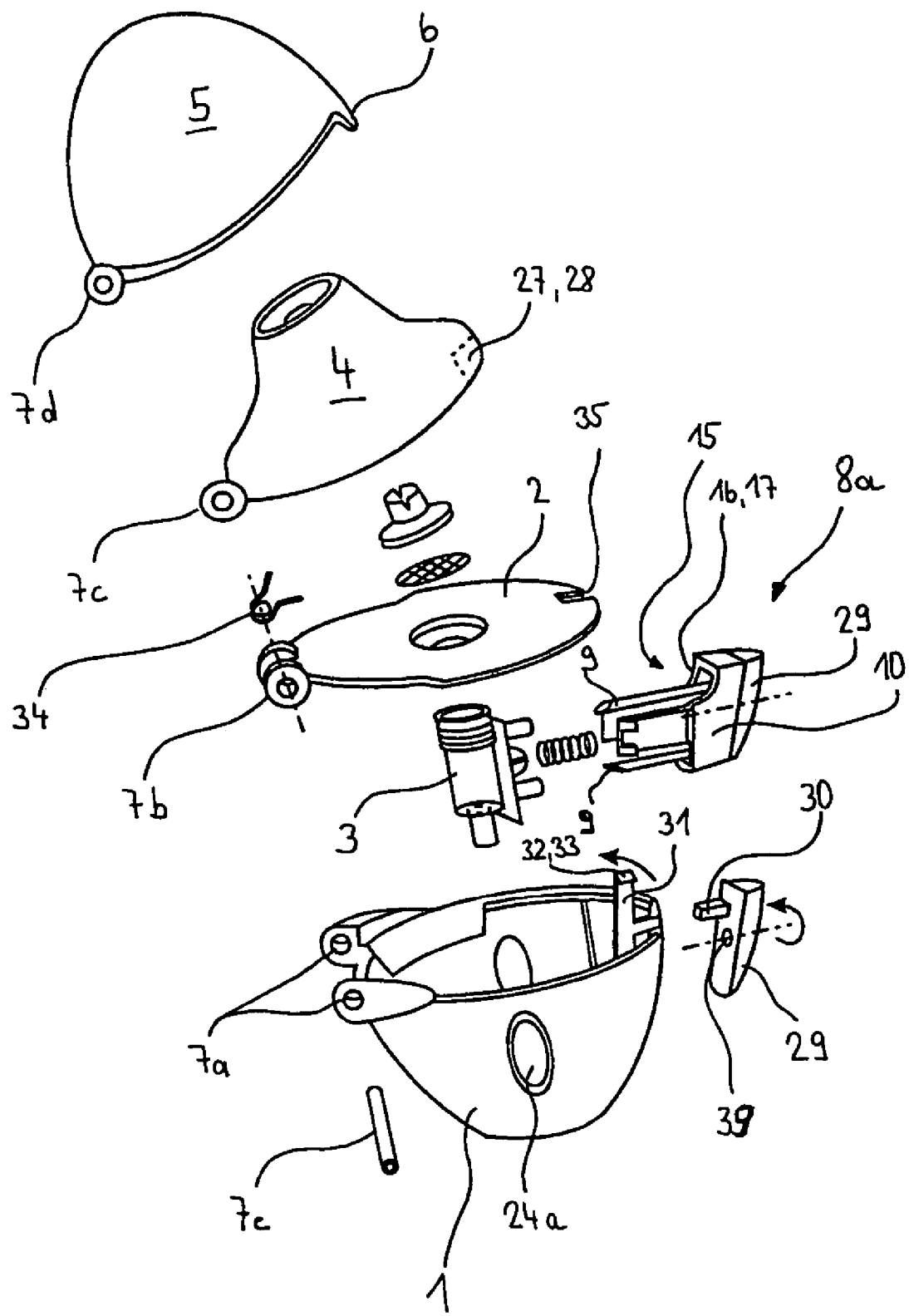
FIG. 3: is an exploded view with multi-functional actuating member of a embodiment with main body and pivot member.

FIG. 3 shows another embodiment in which the mouthpiece 4 is flipped out of the way in a different way. For this purpose the multi-functional actuating member 8*a* is made in two pieces. In addition to the main body 10 which is movably mounted for opening the cover 5, on the exterior thereof, rotatable with respect to the main part 10, is the pivot member 29. The pivot member 29 is fixed centrally on the main part 10 on a peg. Eccentrically mounted above the mounting bore 39 is the impact cam 30 which projects into the interior of the lower part 1 when the inhaler is assembled and when rotated in the direction of the arrow in FIG. 3 comes into contact with the retaining arm 31 pointing vertically upwards. In this way, the upper end 32 of the retaining arm 31 in turn is deflected and the retaining hook 33 provided thereon slides out of the retaining element 27 located in the mouthpiece 4, which is also in the form of a retaining collar 28. To allow the retaining hook 33 to slide unobstructed out of the retaining collar 28, the plate 2 has a retaining arm passage 35 of sufficiently large dimensions.

To close the mouthpiece 4 it is pivoted back into the original position. Thanks to the pointed shape of the retaining hook 33 in the direction of the cover 5 it slides through the retaining arm passage 35 onto the inside of the mouthpiece 4 and there it engages behind the retaining collars 28, as a result of the restoring forces present in the retaining hook 33.

LIST OF REFERENCE NUMERALS

1 lower part
2 plate
3 capsule holder
4 mouthpiece
5 cover
6 closure element
7*a*, 7*b*, 7*c*, 7*d* hinge recesses
7*e* hinge bolt
8 actuating member
8*a* multi-functional actuating member
9 pin
9*a* pin passages
10 main body
11*a*, 11*b* guide arm
12 upper grooved surface
13 lateral grooved surface
14 area nearest the cover
15 recess
16 side wall of the recess
17 sliding surface
18*a*, 18*b* guide sleeve
19 end of the guide arm remote from the main body
20 end stops
21 thrust projection
22 retaining lug
23 front edge thrust projection
24*a* inspection window
24*b* operating window
25 functional elements
26 hook
27 retaining elements
28 retaining collar
29 pivot member
30 impact cam
31 retaining arm
32 upper end of retaining arm
33 retaining hook
34 elastic spring (housing)
35 retaining arm passage
36 hook passage
37 retaining lug opening
38 helical spring
39 mounting bore

The invention claimed is:

1. An inhaler for inhaling powdered medicament from capsules, comprising:
 a lower part(1);
 a plate (2) capable of latching to the lower part (1), wherein the lower part (1) can be closed, and a capsule holder (3) for receiving the capsules which can be be countersunk in the lower part (1);
 a mouthpiece (4) capable of latching to the plate (2);
 a cover (5) which covers the mouthpiece (4) in a closed position and latches it by means of a closure element (6), the lower part (1), the plate (2), the mouthpiece (4) and the cover (5) being jointed to one another by hinge recesses (7*a*, 7*b*, 7*d*) and a hinge bolt (7*e*); and
 an actuating member (8) which can be set in motion from a resting position and thereby co-operates with at least one pin (9) than can be pushed into the capsule holder (3), characterized in that:

the actuating member (8) is constructed as a multi-functional actuating member (8*a*) by means of which, in a first functional position, the closure element (6) can be disengaged from the lower part (1) in order to pivot the cover (5), and with which in a second functional position the mouthpiece (4) engaging with the plate (2) can be released from the plate (2) such that the mouthpiece (4) can be pivoted away from the lower part (1);

the multi-functional actuating member (8*a*) comprises a main body (10) and two parallel guide arms (11*a*, 11*b*) acting thereon;

the guide arms (11*a*, 11*b*) are guided by guide sleeves (18*a*, 18*b*) provided on the outside of the capsule holder (3); and the guide arms (11*a*, 11*b*) comprise, at their end remote from the main body (19), end stops (20) which abut on the guide sleeves (18*a*, 18*b*) in the resting position.

Figure 1A:
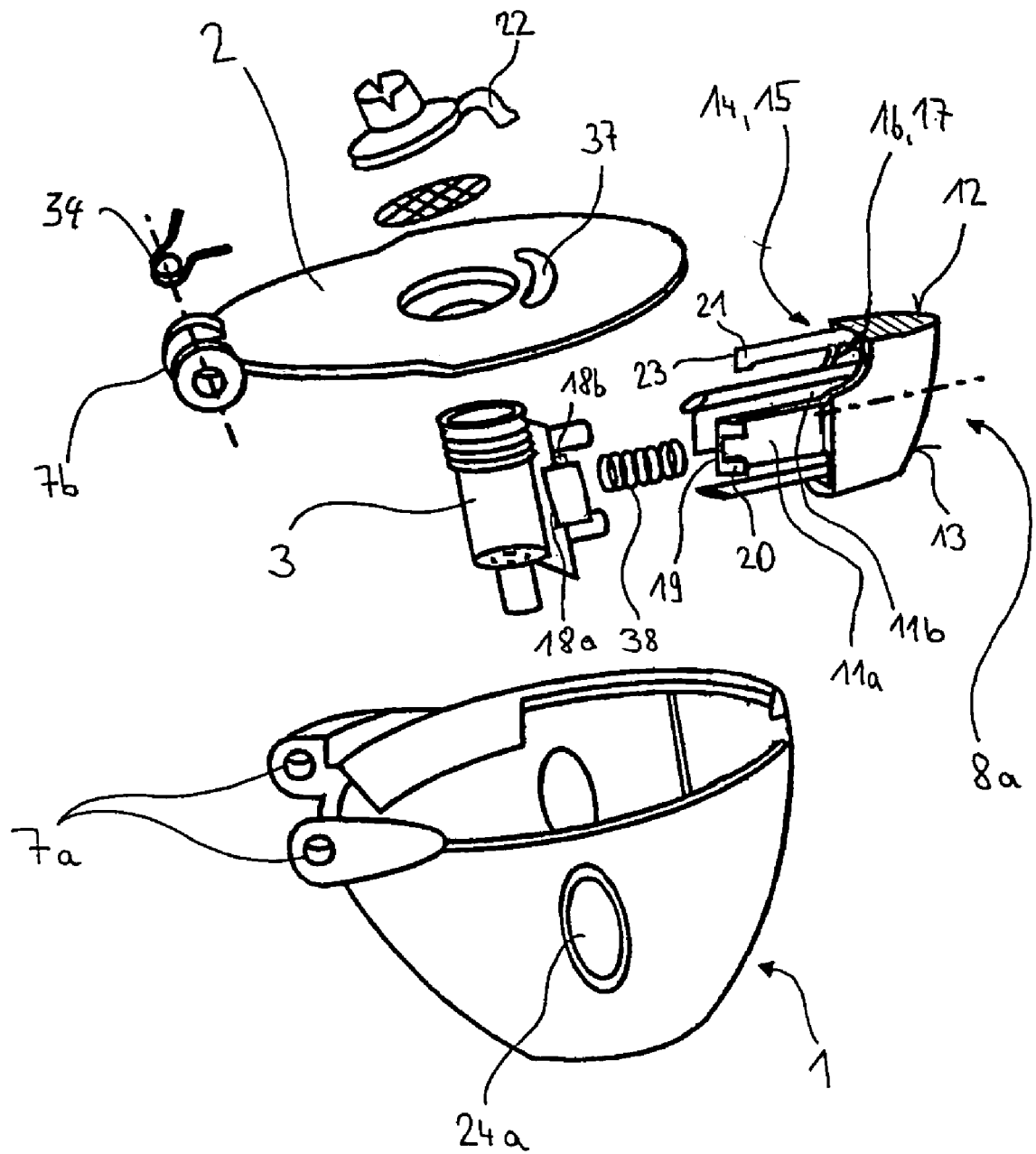
FIG. 1a: is an enlarged detail of the plate, capsule holder and multi-functional actuating member according to FIG. 1.

2. The inhaler according to claim 1, characterized in that the multi-functional actuating member (8*a*) comprises a thrust projection (21) acting on the main body (10) and a retaining lug (22) mounted on the mouthpiece (4) and engaging behind the plate (2), the thrust projection (21) being aligned so that on reaching the second functional position its front edge (23) makes contact with the retaining lug (22) (FIG. 1*a*).

3. The inhaler according to claim 1, characterized in that the multi-functional actuating member (8*a*) comprises a pivot member (29) pivotably mounted on a main body (10), on which is disposed an impact cam (30) projecting into the inhaler, and a retaining arm (31) co-operating with the impact cam (30) and mounted on the lower part, which engages behind the mouthpiece (4) through the plate (2) in the closed position, the impact cam (30) projecting laterally past the retaining arm (31) in the resting position (FIG. 3).

4. The inhaler according to claim 3, characterized in that the impact cam (30) is eccentrically mounted on the pivot member (29).

5. The inhaler according to claim 3, characterized in that the retaining arm (31) comprises a retaining hook (33) on its upper end (32).

6. The inhaler according to claim 4, characterized in that the retaining arm (31) comprises a retaining hook (33) on its upper end (32).

* * * * *